(12) United States Patent
Behler et al.

(10) Patent No.: US 7,405,190 B2
(45) Date of Patent: Jul. 29, 2008

(54) MIXTURES OF FATTY ALCOHOL(S) AND ALK(EN)YL POLYGLYCOSIDE ETHER CARBOXYLATE(S), METHODS FOR THEIR PRODUCTION AND USES THEREOF

(75) Inventors: Ansgar Behler, Bottrop (DE); Karl Heinz Schmid, Mettmann (DE); Michael Neuss, Cologne (DE); Rainer Eskuchen, Langenfeld (DE)

(73) Assignee: Cognis IP Management GmbH, Duesseldorf (DE)

( * ) Notice: Subject to any disclaimer, the term of this patent is extended or adjusted under 35 U.S.C. 154(b) by 155 days.

(21) Appl. No.: 11/088,088

(22) Filed: Mar. 23, 2005

(65) Prior Publication Data

US 2005/0215454 A1 Sep. 29, 2005

(30) Foreign Application Priority Data

Mar. 23, 2004 (DE) ........................ 10 2004 014 013

(51) Int. Cl.
*C11D 3/22* (2006.01)
*C11D 3/20* (2006.01)
*C11D 9/26* (2006.01)
*C11D 11/00* (2006.01)
*C11D 13/00* (2006.01)

(52) U.S. Cl. ........................ 510/474; 510/302; 510/342; 510/353; 510/367; 510/434; 510/437; 510/477; 510/488; 510/491; 510/535

(58) Field of Classification Search ................ 510/302, 510/342, 353, 367, 434, 437, 474, 477, 488, 510/491, 535
See application file for complete search history.

(56) References Cited

U.S. PATENT DOCUMENTS

2004/0047821 A1* 3/2004 Maubru et al. ................ 424/63

2004/0136939 A1* 7/2004 Schmid et al. ........... 424/70.13

FOREIGN PATENT DOCUMENTS

| WO | WO 97/42299 A1 | 11/1997 |
| WO | WO 02/090369 A2 | 11/2002 |
| WO | WO 03/043725 | 5/2003 |
| WO | WO 03/043725 A1 | 5/2003 |

OTHER PUBLICATIONS

Biermann, et al., "Alkylpolyglucoside—Technologie und Eigenschaften", Starch/Stärke, vol. 45, VCH Verlagsgesellschaft mbH, Weinheim, (1993), pp. 281-288.
Salka, "Alkyl Polyglycosides Properties and Applications", Cosmetics & Toiletries, vol. 108, (Mar. 1993), pp. 89-94.
Kahre, et al, "Alkylpolyglycoside—Ein neues Konzept für Pflege und Verträglichkeit in der Kosmetik", SÖFW-Journal, vol. 121, No. 8, (1995), pp. 598, 600-601, 604-611.
Biermann, et al., "Alkylpolyglucoside—Technologie und Eigenschaften", Starch/Stärke, vol. 45, VCH Verlagsgesellschaft mbH, Weinheim, (1993), pp. 281-288, no month given.
Salka, "Alkyl Polyglycosides Properties and Applications", Cosmetics & Toiletries, vol. 108, (Mar. 1993), pp. 89-94.
Kahre, et al, "Alkylpolyglycoside—Ein neues Konzept für Pflege und Verträglichkeit in der Kosmetik", SÖFW-Journal, vol. 121, No. 8, (1995), pp. 598, 600-601, 604-611, Aug. 1995.

* cited by examiner

*Primary Examiner*—Brian P Mruk
(74) *Attorney, Agent, or Firm*—John F. Daniels

(57) ABSTRACT

Mixtures comprising at least one alk(en)yl polyglycoside ether carboxylate, and one or more fatty alcohols are described along with methods for preparing the same, wherein a starting mixture comprising (i) at least one alk(en) yl polyglycoside, and (ii) one or more fatty alcohols is provided, and the starting mixture is reacted with a compound selected from the group consisting of $\omega$-halocarboxylic acids, $\omega$-halocarboxylic acid salts, $\omega$-halocarboxylic acid esters, and mixtures thereof.

18 Claims, No Drawings

MIXTURES OF FATTY ALCOHOL(S) AND ALK(EN)YL POLYGLYCOSIDE ETHER CARBOXYLATE(S), METHODS FOR THEIR PRODUCTION AND USES THEREOF

BACKGROUND OF THE INVENTION

Alk(en)yl polyglycoside ether carboxylates are known surfactants. Alk(en)yl polyglycoside ether carboxylate refers to alkyl polyglycoside ether carboxylate and/or alkenyl polyglycoside ether carboxylate. Alk(en)yl polyglycoside ether carboxylates can be obtained by derivatizing alk(en)yl polyglycoside (alk(en)yl polyglycoside refers to alkyl polyglycoside and/or alkenyl polyglycoside) at one or more OH groups of the polyglycoside component of the alk(en)yl polyglycoside by reaction of each of these one or more OH groups with one molecule of ω-halocarboxylic acid or a salt or ester thereof to form an ether and conversion of the carboxylic acid group of the ω-halocarboxylic acid into a carboxylate group.

The alk(en)yl polyglycoside from which the alk(en)yl polyglycoside ether carboxylates can be obtained in the described manner is known as the "alk(en)yl polyglycoside on which the alk(en)yl polyglycoside ether carboxylate is based". The substituents of the alk(en)yl polyglycoside ether carboxylate which are derived from ω-halocarboxylic acid are called "ether carboxyl groups".

The number of ether carboxyl groups bearing one molecule of alk(en)yl polyglycoside ether carboxylate in a certain sample of alk(en)yl polyglycoside ether carboxylate is different and is determined by the production process. In a certain sample of alk(en)yl polyglycoside ether carboxylate containing a certain statistical average of ether carboxyl groups pre molecule of alk(en)yl polyglycoside ether carboxylate, the number of ether carboxyl groups per molecule of alk(en)yl polyglycoside ether carboxylate varies from molecule to molecule.

Alk(en)yl polyglycoside ether carboxylates are normally riot pure substances because different fatty alcohol residues, different chain lengths of the polyglycoside units and different degrees of substitution with ether carboxylate groups are usually present in one and the same sample. Where reference is made to alk(en)yl polyglycoside ether carboxylate in the singular, this does not mean that the substance is pure.

Alk(en)yl polyglycosides can be represented by formula (I) below:

$$R^1O\text{-}[G]_p \qquad (I)$$

in which $R^1$ is an alkyl group or an alkenyl group preferably containing 4 to 22 carbon atoms, G is a sugar unit preferably containing 5 or 6 carbon atoms and p is preferably a number of 1 to 10. Alk(en)yl polyglycosides can be produced by standard methods. The production of alk(en)yl polyglycosides is described, for example, in the article by Biermann et al. in Starch/Stärke 45, 281 (1993), in the article by B. Salka in Cosm. Toil. 108, 89 (1993) and in the article by J. Kahre et al. in SÖFW-Journal, No. 8, 598 (1995).

In the production of alk(en)yl polyglycosides, the fatty alcohol is generally used in excess and, after the reaction, is completely removed from the product by distillation or its content in the product mixture is reduced by distillation.

After the reaction, but before distillation, the "crude alk(en)yl polyglycoside" normally contains ca. 50 to 80% of fatty alcohol.

Alk(en)yl polyglycoside ether carboxylate can be produced by reaction of alk(en)yl polyglycoside with ω-halocarboxylic acids in an alkaline medium. Since alk(en)yl polyglycosides have very high viscosities in the molten state, suitable solvents are normally added during the reaction. Organic aprotic solvents are generally used, so that hydrolysis of the halocarboxylic acids or salts or esters thereof is avoided. WO 97/42299 describes the reaction with toluene as solvent.

WO 02/090369 discloses a process for the production of alk(en)yl polyglycoside ether carboxylate by reaction of alk(en)yl polyglycoside with an ω-halocarboxylic acid, a salt or ester thereof in aqueous solution. WO 03/043725 discloses mixtures of alk(en)yl polyglycoside and fatty alcohols and their use. Mixtures of alk(en)yl polyglycoside ether carboxylate and fatty alcohols are unknown in the prior art.

SUMMARY OF THE INVENTION

This invention relates, in general, to mixtures containing one or more different fatty alcohols and an alk(en)yl polyglycoside ether carboxylate, to processes for the production of such mixtures and to their use. The present invention also relates to a process for the production of alk(en)yl polyglycoside ether carboxylates from the mixture according to the invention containing one or more different fatty alcohols and an alk(en)yl polyglycoside ether carboxylate. The problem addressed by the present invention was to provide other surfactant mixtures having advantageous properties.

This problem has been solved by a mixture containing
(a) alk(en)yl polyglycoside ether carboxylate, the counterions to the alk(en)yl polyglycoside ether carboxylate anions preferably being alkali metal cations, more particularly sodium cations, and
(b) one or more different fatty alcohols.

This mixture is a subject of the present invention and is called the mixture according to the invention.

One embodiment of the invention is the mixture according to the invention in which the alk(en)yl polyglycoside ether carboxylate makes up from 10 to 90% by weight, preferably from 20 to 80% by weight and more particularly from 20 to 60% by weight of the mixture.

Another embodiment of the invention is the mixture according to the invention in which the fatty alcohol makes up from 10 to 90% by weight, preferably from 20 to 80% by weight and more particularly from 40 to 80% by weight of the mixture.

Another embodiment of the invention is the mixture according to the invention in which the alk(en)yl polyglycoside on which the alk(en)yl polyglycoside ether carboxylate is based corresponds to formula (I):

$$R^1O\text{-}[G]_p \qquad (I)$$

in which $R^1$ is an alkyl group or an alkenyl group containing 4 to 22 carbon atoms and preferably 8 to 18 carbon atoms ($R^1$ is preferably a mixture of hexadecyl groups and octadecyl groups), G is a sugar unit containing 5 or 6 carbon atoms (sugar units G are preferably derived from aldoses or ketoses containing 5 to 6 carbon atoms, more particularly from glucose) and p is a number of 1 to 10 (preferably 1.1 to 3). The index p in general formula (I) indicates the degree of oligomerization (DP), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alk(en)yl polyglycosides having an average degree of oligomerization p of 1.1 to 3.0 are preferably used. Alk(en)yl polyglycosides having a degree of oligomerization of less than 1.7 and, more particularly, between 1.2 and 1.4 are preferred from the applicational point of view.

Another embodiment of the invention is the mixture according to the invention in which the fatty alcohols are a mixture of $C_{8-20}$ and preferably $C_{14-20}$ fatty alcohols.

Another subject of the present invention is a process for the production of the mixture according to the invention which comprises reacting a starting mixture containing (a) the alk(en)yl polyglycoside on which the alk(en)yl polyglycoside ether carboxylate is based and (b) one or more different fatty alcohols with a compound selected from the group consisting of an ω-halocarboxylic acid, a salt (preferably an alkali metal salt and more particularly the sodium salt) of an ω-halocarboxylic acid or an ester of an ω-halocarboxylic acid. This process is called the process according to the invention.

One embodiment of the invention is the process according to the invention where the reaction is carried out in the presence of a base (preferably sodium hydroxide or potassium hydroxide, more particularly sodium hydroxide).

Another embodiment of the invention is the process according to the invention where the ω-halocarboxylic acid, the salt of an ω-halocarboxylic acid or the ester of an ω-halocarboxylic acid is a compound containing 2 to 10, preferably 2 to 6 and more particularly 2 carbon atoms (sodium monochloroacetate is particularly preferred).

Another embodiment of the invention is the process according to the invention where the percentage content of d (i.e. fatty alcohols), based on the sum of c and d, is from 10 to 80% by weight and preferably from 40 to 80% by weight.

Another embodiment of the invention is the process according to the invention where the molar ratio of the compound selected from the group consisting of an ω-halocarboxylic acid, the salt of an ω-halocarboxylic acid and the ester of an ω-halocarboxylic acid to the alk(en)yl polyglycoside on which the alk(en)yl polyglycoside ether carboxylate is based is 0.5:1 to 3.5:1 and preferably 1:1 to 2.5:1.

Another embodiment of the invention is the process according to the invention where the reaction is carried out at 50 to 130° C. and preferably at 80 to 110° C.

Another embodiment of the invention is the process according to the invention where the reaction is carried out in the absence of solvent (apart from the fatty alcohols d present).

Another subject of the present invention is the use of the mixture according to the invention for the production of cosmetic or pharmaceutical preparations.

Another subject of the present invention is a process for the production of alk(en)yl polyglycoside ether carboxylate comprising (a) the process according to the invention and (b) removing the fatty alcohols from the mixture, the fatty alcohols preferably being removed from the mixture by distillation.

It has surprisingly been found that the reaction of alk(en)yl polyglycoside with a compound selected from the group consisting of an ω-halocarboxylic acid, the salt of an ω-halocarboxylic acid and the ester of an ω-halocarboxylic acid can be carried out in the absence of water or other solvents providing the alk(en)yl polyglycoside is used as a mixture containing the alk(en)yl polyglycoside and one or more different fatty alcohols. The so-called "crude alk(en)yl polyglycoside", which is obtained in the production of the alk(en)yl polyglycoside before the fatty alcohol is removed by distillation and which preferably contains 50 to 80% by weight of fatty alcohol, is preferably used. It has been found in this connection that the alk(en)yl polyglycoside reacts almost exclusively with the compound selected from the group consisting of an ω-halocarboxylic acid, the salt of an ω-halocarboxylic acid or the ester of an ω-halocarboxylic acid to form alk(en)yl polyglycoside ether carboxylate and the fatty alcohol leaves the reaction almost or completely unchanged.

DETAILED DESCRIPTION OF THE INVENTION

An advantage of the process according to the invention for the production of alk(en)yl polyglycoside ether carboxylate is that the crude alk(en)yl polyglycoside from the production of alk(en)yl polyglycoside can be used without the fatty alcohol having to be removed beforehand. In addition, no solvents are required.

The mixture according to the invention may be used as a surfactant in surface-active preparations such as, for example, laundry and dishwashing detergents, household cleaners and cosmetic and/or pharmaceutical preparations. These surface-active preparations may contain pearlizing waxes, consistency factors, thickeners, superfatting agents, stabilizers, silicone compounds, fats, waxes, lecithins, phospholipids, antioxidants, deodorants, antiperspirants, antidandruff agents, swelling agents, tyrosine inhibitors, hydrotropes, solubilizers, preservatives, perfume oils, dyes, other surfactants and the like as further auxiliaries and additives. The cosmetic and/or pharmaceutical preparations may be, for example, oral hygiene and dental care preparations, hair shampoos, hair lotions, foam baths, shower baths, creams, gels, lotions, alcoholic and aqueous/alcoholic solutions and emulsions.

The mixtures according to the invention containing alk(en)yl polyglycoside ether carboxylate and one or more different fatty alcohols are suitable for the applications disclosed in WO 03/043725 for the mixtures according to WO 03/043725. More particularly, these applications are in cosmetic or pharmaceutical formulations.

EXAMPLES

In the Examples, percentages represent % by weight.

C16/18 alk(en)yl polyglycoside was used for the Examples. This is an alk(en)yl polyglycoside which is obtained by the reaction of glucose with C14/20 fatty alcohol. C14/20 fatty alcohol is a mixture of various fatty alcohols with the following composition:

| | |
|---|---|
| C14 fatty alcohol: | max. 3% |
| C16 fatty alcohol: | 45-55% |
| C18 fatty alcohol: | 45-55% |
| C20 fatty alcohol: | max. 3% |

The residual fatty alcohol content in the C16/18 alk(en)yl polyglycoside was 59.5%.

Example 1

Production of C16/18 alk(en)yl polyglycoside ether carboxylate

In a reaction vessel, 749.1 g of C16/18 alk(en)yl polyglycoside with a residual fatty alcohol content (as above) of 78% (0.33 mol) and 22.4 g of sodium hydroxide microprills (0.56 mol) were heated to a temperature of 85° C. 65.3 g of sodium chloroacetate (0.56 mol) were then added dropwise with stirring over a period of 4 hours. Following an after-reaction time of 3 hours, the theoretical quantities of chloride (2.32% Cl) having been released, the reaction was terminated.

The following analytical data were determined:
fatty alcohol content in the alk(en)yl polyglycoside ether carboxylate: 64.5%
NaCl content: 3.6%
unreacted alk(en)yl polyglycoside in the product mixture: 5.50% (this corresponds to a conversion of 72.1%)

Example 2

Production of C16/18 alk(en)yl polyglycoside ether carboxylate

In a reaction vessel, 500.0 g of C16/18 alk(en)yl polyglycoside with a fatty alcohol content (as above) of 64.1% (0.37 mol) and 19.1 g of sodium hydroxide microprills (0.48 mol) were heated to a temperature of 115° C. 55.7 g of sodium chloroacetate (0.48 mol) were then added with stirring. Following an after-reaction time of 4 hours, the theoretical quantities of chloride (2.94% Cl) having been released, the reaction was terminated.
The following analytical data were determined:
fatty alcohol content in the alk(en)yl polyglycoside ether carboxylate: 53.0%
NaCl content: 4.8%
unreacted alk(en)yl polyglycoside in the product mixture: 6.6% (this corresponds to a conversion of 78.8%)

Example 3

Production of C16/18 alk(en)yl polyglycoside ether carboxylate

In a reaction vessel, 493.4 g of C16/18 alk(en)yl polyglycoside (0.4 mol) with a fatty alcohol content of 59.5% and 27.2 g of sodium hydroxide microprills (0.68 mol) were heated to a temperature of 100° C. 79.2 g of sodium chloroacetate (0.68 mol) were then added in portions with stirring over a period of 4 hours. Following an after-reaction time of 3 hours, the theoretical quantities of chloride (3.95% Cl) having been released, the reaction was terminated.
The following analytical data were determined:
fatty alcohol content in the alk(en)yl polyglycoside ether carboxylate: 52.2%
NaCl content: 6.5% unreacted alk(en)yl polyglycoside in the product mixture: 5.0% (this corresponds to a conversion of 85%)

What is claimed is:

1. A mixture comprising: (a) at least one alk(en)yl polyglycoside ether carboxylate; and (b) one or more fatty alcohols, which fatty alcohols consist of $C_8$-$C_{20}$ alcohols.

2. The mixture according to claim 1, wherein the at least one alk(en)yl polyglycoside ether carboxylate is present in an amount of from 10 to 90% by weight, and the one or more fatty alcohols is present in an amount of from 10 to 90% by weight, based on the mixture.

3. The mixture according to claim 1, wherein the at least one alk(en)yl polyglycoside ether carboxylate is present in an amount of from 20 to 80% by weight, and the one or more fatty alcohols is present in an amount of from 20 to 80% by weight, based on the mixture.

4. The mixture according to claim 1, wherein the at least one alk(en)yl polyglycoside ether carboxylate is present in an amount of from 20 to 60% by weight, and the one or more fatty alcohols is present in an amount of from 40 to 80% by weight, based on the mixture.

5. The mixture according to claim 1, wherein the at least one alk(en)yl polyglycoside ether carboxylate is derived from an alk(en)yl polyglycoside corresponding to the general formula (I):

$$R^1O\text{-}[G]_p \quad (I)$$

wherein $R^1$ represents an alkyl or alkenyl group having from 4 to 22 carbon atoms, G represents a sugar unit having 5 or 6 carbon atoms and p represents a number of from 1 to 10.

6. The mixture according to claim 1, wherein the one or more fatty alcohols consists of a mixture of two or more $C_{14\text{-}20}$ alcohols.

7. The mixture according to claim 1, wherein the one or more fatty alcohols consists of a mixture of $C_{16}$ and $C_{18}$ alcohols.

8. The mixture according to claim 1, wherein the one or more fatty alcohols consists of a mixture of $C_{14}$, $C_{16}$, $C_{18}$, and $C_{20}$ alcohols.

9. A mixture comprising:
(a) at least one alk(en)yl polyglycoside ether carboxylate, wherein the at least one alk(en)yl polyglycoside ether carboxylate is derived from an alk(en)yl polyglycoside corresponding to the general formula (I):

$$R^1O\text{-}[G]_p \quad (I)$$

wherein $R^1$ represents an alkyl or alkenyl group having from 4 to 22 carbon atoms, G represents a sugar unit having 5 or 6 carbon atoms and p represents a number of from 1 to 10; and
(b) one or more fatty alcohols, wherein the one or more fatty alcohols consist of a mixture of $C_{16}$ and $C_{18}$ alcohols;
wherein the at least one alk(en)yl polyglycoside ether carboxylate is present in an amount of from 20 to 60% by weight, and the one or more fatty alcohols is present in an amount of from 40 to 80% by weight, based on the mixture.

10. A cosmetic or pharmaceutical preparation comprising a mixture according to claim 1.

11. A process comprising:
(a) providing a starting mixture comprising (i) at least one alk(en)yl polyglycoside, and (ii) one or more fatty alcohols present in an amount of from 10 to 80% by weight of the starting mixture; and
(b) reacting the starting mixture with a compound selected from the group consisting of ω-halocarboxylic acids, ω-halocarboxylic acid salts, ω-halocarboxylic acid esters, and mixtures thereof.

12. The process according to claim 11, wherein the starting mixture is reacted with the compound in the presence of a base.

13. The process according to claim 11, wherein the compound has from 2 to 10 carbon atoms.

14. The process according to claim 11, wherein the alk(en)yl polyglycoside corresponds to the general formula (I):

$$R^1O\text{-}[G]_p \quad (I)$$

wherein $R^1$ represents an alkyl or alkenyl group having from 4 to 22 carbon atoms, G represents a sugar unit having 5 or 6 carbon atoms and p represents a number of from 1 to 10.

15. The process according to claim 11, wherein the one or more fatty alcohols comprises a mixture of two or more $C_{8\text{-}20}$ alcohols.

16. The process according to claim 14, wherein the one or more fatty alcohols comprises a mixture of two or more $C_{8\text{-}20}$ alcohols.

17. The process according to claim 11, wherein the compound and the alk(en)yl polyglycoside are reacted in a molar ratio of from 0.5:1 to 3.5:1.

18. The process according to claim 11, wherein the one or more fatty alcohols is present in an amount of from 40 to 80% by weight of the starting mixture.

* * * * *